United States Patent
Zakoshansky et al.

(10) Patent No.: US 6,252,124 B1
(45) Date of Patent: Jun. 26, 2001

(54) WASTELESS ECONOMIC METHOD OF PRODUCTION OF PHENOL AND ACETONE

(75) Inventors: Vladimir Mikhailovitch Zakoshansky, Mt. Vernon, IN (US); Irina Ivanovna Vassilieva, St. Petersburg (RU)

(73) Assignee: ILLA International, LLC, Reno, NV (US)

( * ) Notice: Subject to any disclaimer, the term of this patent is extended or adjusted under 35 U.S.C. 154(b) by 0 days.

(21) Appl. No.: 09/301,605

(22) Filed: Apr. 29, 1999

(30) Foreign Application Priority Data

Sep. 24, 1998 (RU) .................................. 96120810

(51) Int. Cl.⁷ .................................... C07C 37/08
(52) U.S. Cl. ........................ 568/798; 568/385; 568/735
(58) Field of Search .................................. 568/385, 798, 568/735; 585/435

(56) References Cited

U.S. PATENT DOCUMENTS

| | | | |
|---|---|---|---|
| 4,358,618 | * 11/1982 | Sifniades et al. ..................... | 568/385 |
| 5,017,729 | * 5/1991 | Fukuhara et al. ..................... | 568/798 |
| 5,254,751 | * 10/1993 | Zakoshansky et al. .............. | 568/385 |
| 5,530,166 | * 6/1996 | Zakoshansky et al. .............. | 568/798 |

\* cited by examiner

*Primary Examiner*—Sreeni Padmanabhan
(74) *Attorney, Agent, or Firm*—Edward Etkin, Esq.

(57) ABSTRACT

A new phenol and acetone production process reduces the amount of necessary stages for obtaining phenol and acetone, results in higher yield of desired products and requires less complex equipment implementation and less energy than current processes of a similar type. The new process comprises a stage of cumene hydroperoxide production via cumene oxidation, a stage of cumene oxidation products concentration to produce technical cumene hydroperoxide and recycle of unreacted cumene to oxidation stage after treatment, a stage of separation of cumene oxidation products in a continuous or cycle adsorption-desorption with the purpose of producing CHP that is free from DMBA and AP utilizing predetermined adsorbents and desorbents, a stage of heterogeneous or homogeneous cumene hydroperoxide cleavage with the use of acidic catalysts to produce at least phenol and acetone, a stage of AP fractionation from AP-cumene fraction and return of cumene to the separation stage, a stage of catalytic DMBA hydrogenation into cumene, and a stage of separating phenol, acetone, and desorbent to produce required product phenol and acetone. This results in (1) elimination of formation of by-products at the CHP cleavage stage and the fractionation stage; (2) simplification and reduced complexity of CHP cleavage products fractionation; and (3) a significant decrease in energy expenses compared to the conventional phenol and acetone production processes.

11 Claims, 5 Drawing Sheets

1. cumene oxidation to CHP a) main reaction
$$Cumene + O_2 \longrightarrow CHP$$

b) side-reactions:
$$Cumene + O_2 \longrightarrow AP$$
$$Cumene + O_2 \longrightarrow DMBA$$
$$Cumene + O_2 \longrightarrow DCP\ (dicumylperoxide)$$

2. acidic-catalytic cleavage of oxidation products:

a) main reaction
$$CHP \xrightarrow{H^+} Phenol + Acetone$$

b) side reactions
$$DMBA \rightleftarrows AMS + H_2O$$
$$CHP + DMBA \rightleftarrows DCP + H_2O$$

$$DMBA \begin{array}{l} \nearrow AMS\ dimers \\ \rightarrow Complex \\ \searrow Deep\ condensation\ products \end{array} \Bigg\} phenol\ tar$$

where DCP - dicumylperoxide 3. catalyst neutralization
$$H_2SO_4 + NaOH \longrightarrow Na_2SO_4$$

4. partial cracking of phenol tar
$$phenol\ tar \longrightarrow phenol + AMS + \text{«heavy tar»}$$

5. AMS hydrogenation to cumene
$$AMS + H_2 \xrightarrow{catalyst} cumene$$

6. removal of microimpurities from phenol
$$HA + phenol \xrightarrow{H^+} 2MBF \longrightarrow tar$$
$$AMS \xrightarrow{H^+} tar$$

$$carbonyl\ compounds \longrightarrow tar$$

where HA - hydroxyacetone, 2-MBF - 2-methylbenzofuran 7. removal of microimpurities from acetone
$$aldehydes\ C_1\text{-}C_3 \xrightarrow{NaOH} aldol$$

Traditional Stage 1. cumene oxidation to CHP a) main reaction

Cumene + O$_2$ $\longrightarrow$ CHP b) side-reactions:

Cumene + O$_2$ $\longrightarrow$ AP
Cumene + O$_2$ $\longrightarrow$ DMBA
Cumene + O$_2$ $\longrightarrow$ DCP (dicumylperoxide)

New Stage 2: separation of technical CHP (cumene oxidation products) Into components by method of continuous or cycle adsorption-desorption Stage 3: acidic (heterogeneous or homogeneous) CHP cleavage to phenol and acetone:

CHP $\xrightarrow{H^+}$ Phenol + Acetone

New Stage 4: hydrogenation of DMBA separated from oxidation products at the stage of continuous adsorption-desorption to cumene:

DMBA + H$_2$ $\longrightarrow$ cumene

WASTELESS ECONOMIC METHOD OF PRODUCTION OF PHENOL AND ACETONE

BACKGROUND OF THE INVENTION

The present invention is directed to a method for producing phenol and acetone in which: (1) no side-products are formed due to production of cumene hydroperoxide (CHP); (2) the products are free from dimethyl benzene alcohol (DMBA); (3) the selectivity at cleavage stage approaches the theoretical level of 100%; (4) the stage of product fractionation is greatly simplified due to the production of technical CHP free from acetophenone (AP), DMBA, alpha-methylstyrene (AMS) and products of their conversion; (5) the energy expenses are reduced at least 1.5–2 times; (6) the process construction and technology are substantially simplified; and (7) capital costs for fractionation stage are significantly decreased.

There are numerous patents that refer to various methods for improving the parameters of important commercial process of phenol and acetone production. These patents include, but are not limited to: U.S. Pat. No. 2,663,740; U.S. Pat. No. 4,358,618; U.S. Pat. No. 5,254,751; U.S. Pat. No. 5,530,166; U.S. Pat. No. 5,510,543; and U.S. Pat. No. 5,502,259.

Without exception, the phenol and acetone production processes and methodology taught and disclosed by these patents are generally based on one or more of the following principles:

1. Oxidation of cumene to cumene hydroperoxide to produce the oxidation products containing from 20 to 40% CHP;
2. Concentration of oxidation products by distilling unreacted cumene under vacuum in one, two or sometimes three steps and then directing the recycle to oxidation stage while being pretreated from impurities;
3. Homogeneous cleavage in phenol-acetone-cumene medium using sulfuric acid as a catalyst to produce phenol, acetone, alpha-methylstyrene and by-products (for example, the "phenol tar" which is hard to utilize commercially);
4. Neutralization of sulfuric acid in CHP cleavage products by alkaline agents and removal of salts from the above named products (e.g. $Na_2SO_4$, $NaHSO_4$);
5. Fractionation of cleavage products to produce phenol, acetone, AMS and phenol tar;
6. Hydrogenation of AMS obtained at CHP cleavage stage to convert it into cumene and further recycling cumene to the oxidation stage;
7. Phenol purification from micro impurities with the use of acidic ion-exchange resins;
8. Acetone treatment from impurities with the use of alkalis; and
9. Implementation of a stage of partial thermal cracking of production wastes or their incineration to produce steam.

From the chemical view point, the vast majority of previously known (hereinafter "conventional") processes of phenol and acetone production via the cumene method that exist in the industry and in patent and other literature, can be characterized by the chemical reactions shown in FIG. 1

It is readily apparent to one skilled in the art that the main objective of the designers of this commonly-used process was in finding a way to increase the yield of desired by-product AMS at a CHP cleavage stage (after the ultimate selectivity of 94–95 % theoretical was obtained at cumene oxidation stage).

Two different technologies ("UOP" disclosed in U.S. Pat. No. 4,358,618, and "FAN" disclosed in U.S. Pat. Nos. 5,254,751 and 5,530,166) succeeded in achieving an AMS yield at commercial unit at a level of 80% theoretical. The yield of phenol tar was minimized down to approximately 35 kg/t phenol when cumene usage per 1 ton of phenol was 1307–1310 kg (taking into account the stage of phenol tar cracking) and minimized to 55–58 kg/t and cumene usage of approximately 1330 kg per ton of phenol without phenol tar cracking.

Figure 2:
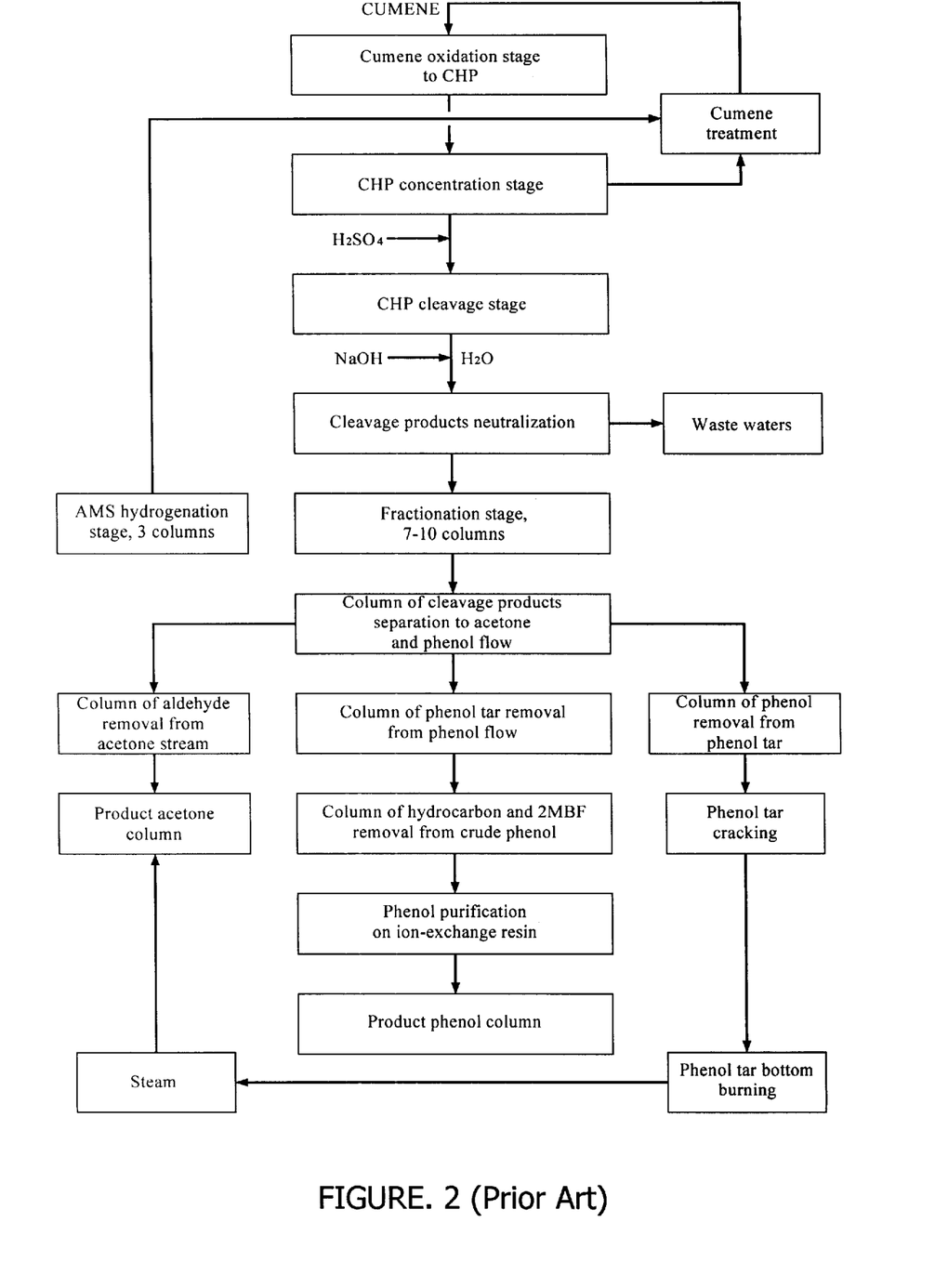
FIG. 2 schematically shows a diagram of a prior art conventional process for producing acetone and phenol via the traditional cumene method.

Thus, even the best above-indicated technologies result in losses of initial feed cumene from 33 kg/t to 53 kg/t while the yield of non-utilized wastes remains high. Finally, large number of chemical stages increases the complexity of required implementation technology and further requires increased energy expenditures. Referring now to FIG. 2, a diagram of a typical implementation of conventional technology as described above is shown. This typical implementation is described in whole or in part in the following U.S. patents: U.S. Pat. No. 2,663,740; U.S. Pat. No. 4,358,618; U.S. Pat. No. 5,254,751; U.S. Pat. No. 5,502,259; U.S. Pat. No. 5,510,543; U.S. Pat. No. 5,530,166.

It should be noted that it is nearly impossible to obtain 100% AMS yield utilizing conventional technology due to existing equilibrium of reaction DMBA$\Leftrightarrow$ AMS+H2O and due to formation of AMS dimers and complex phenols form DMBA. With current technology it is also impossible to avoid complexity and high energy requirements of CHP cleavage products fractionation as such products contain AMS, acetophenone and other impurities such as mesityl oxide, hydroxyacetone and others.

Each of the patents mentioned above in connection with FIG. 1 provides some innovation to one or several of the stages of the process of FIG. to improve the parameters and overall results of the process. However, the basic chemistry of the process and its implementation in terms of required equipment remain unchanged.

It would thus be desirable to provide an improved chemical process that reduces the amount of necessary stages for obtaining phenol and acetone via the cumene method. It would also be desirable to provide a new process that results in higher yield of desired products and by-products. It would further be desirable to provide a chemical process that requires less complex equipment implementation than current processes of similar type. It would finally be desirable to provide a chemical process that had significantly lower energy requirements.

SUMMARY OF THE INVENTION

The novel chemical process of the present invention reduces the amount of necessary stages for obtaining phenol and acetone (from 7 to 4), results in higher yield of desired products and requires less complex equipment implementation and less energy than current processes of a similar type. At the outset it should be noted that the words "reaction" and "stage" are used interchangeably.

The basis of the improved process is a complete separation of technical CHP into components present therein by a method of continuous adsorption-desorption. This approach eliminates from the following reactions from the previously known series of chemical reactions: (1) all DMBA and CHP+DMBA side reactions at a CHP cleavage stage; (2) the entire neutralization stage if the cleavage stage is conducted using heterogeneous or homogenous catalysts; (3) the entire stage of phenol tar cracking and all related occurring desired and undesired reactions; (4) the hydrogenation stage of AMS to cumene; and (5) stages of removal of micro impurities from phenol and acetone. Furthermore, the process of the present invention eliminates the need for complex preparation of feed to A.M. hydrogenation.

In summary, the novelty of the chemical reactions and technological implementation of the improved process of the present invention may be characterized by the following:

1. Cleavage of CHP that does not contain DMBA, AP and DCP, elimination of all chemical reactions that form side products;
2. Hydrogenation of DMBA separated from cumene oxidation products to cumene;
3. Production of CHP that is free from DMBA, AP and other impurities conducted by a method of continuous adsorption-desorption;
4. DMBA hydrogenation to cumene; and
5. The use of initial process feed (i.e. cumene) as a desorbent and its further recycle to CHP production stage.

Advantages of the improved process of the present invention include, but are not limited to the following:

1. Elimination of formation of by-products at the CHP cleavage stage and the fractionation stage;
2. Significant simplification and reduced complexity of equipment necessary for the CHP decomposition stage;
3. Simplification and reduced complexity of CHP cleavage products fractionation (i.e. the number of rectification columns at the fractionation stage can be reduced by a factor of 2 in accordance with the present invention as compared to the conventional scheme); and
4. A significant decrease in energy expenses compared to the conventional scheme (by a factor of approximately 1.5–2).

The various features of novelty which characterize the invention are pointed out with particularity in the claims appended to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

In the drawings, wherein like reference characters denote corresponding or similar elements throughout the various figures.

DESCRIPTION OF THE PREFERRED EMBODIMENT

The basis of the improved process of the present invention is a complete separation of technical CHP into components present therein by a method of continuous adsorption-desorption. The process of the present invention reduced the number of reactions necessary in previously known processes as shown in FIG. 1. The improved process of the present invention eliminates all DMBA side reactions 2(b) at a CHP cleavage stage (FIG. 1), eliminates a neutralization stage (reaction 3, FIG. 1) if the cleavage stage is conducted on heterogeneous catalysts, eliminates the stage of phenol tar cracking and all occurring desired and undesired reactions (reaction 4, FIG. 1), eliminates reactions 5, 6 and 7 (FIG. 1), and eliminates complex preparation of feed to AMS hydrogenation.

Figure 1:
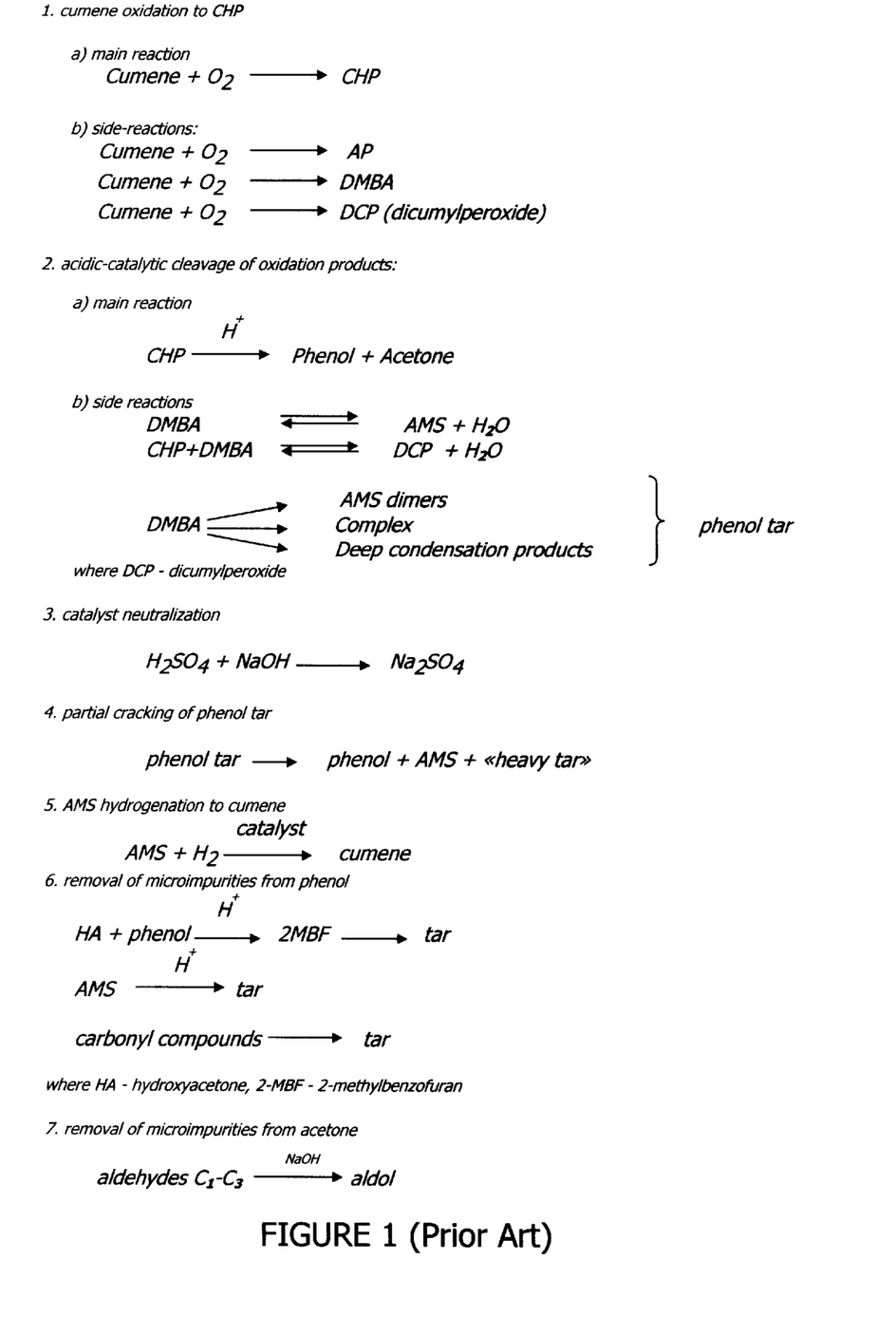
FIG. 1 shows a series of prior art chemical reactions representative of a conventional process for producing acetone and phenol via the cumene method.
Figure 3:
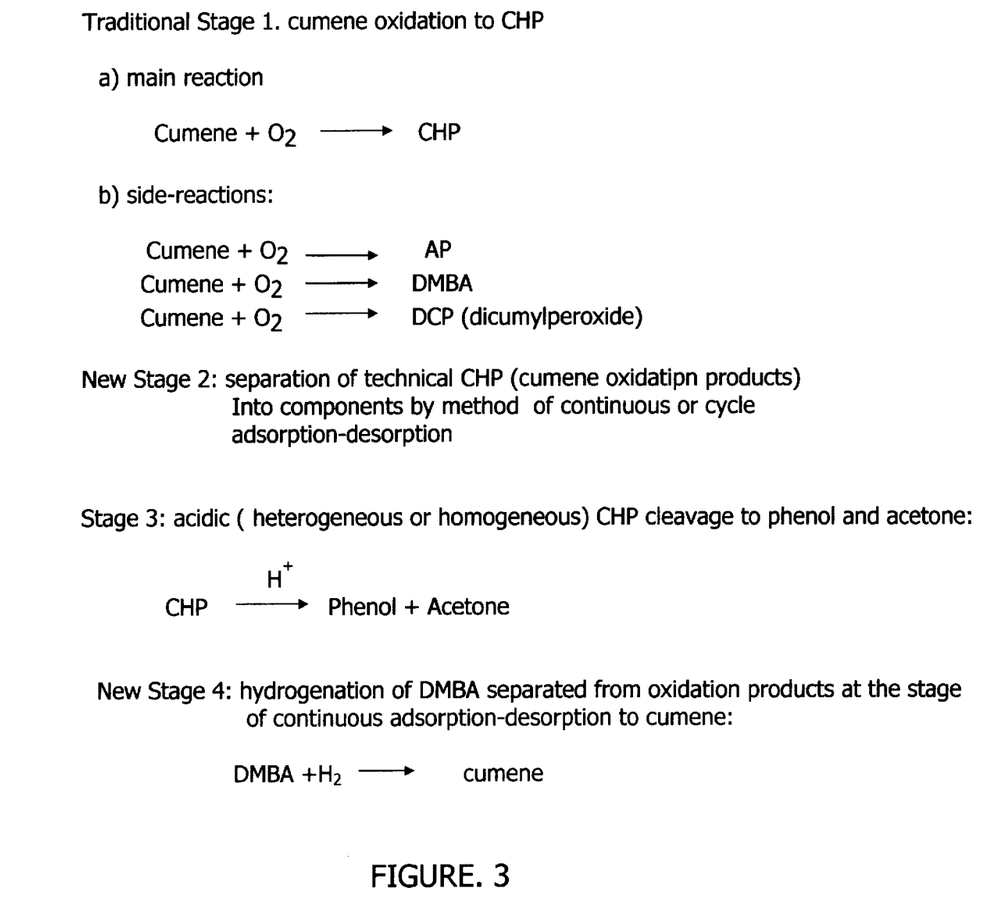
FIG. 3 shows a series of chemical stages representative of the improved process for producing acetone and phenol via the cumene method in accordance with the present invention.

Referring now to FIG. 3, the new process of the present invention includes a cumene oxidation stage—Traditional Stage 1—which is carried out as usual (i.e. in the same manner as reaction/stage 1 of FIG. 1), and a stage of acidic (heterogeneous or homogeneous) CHP cleavage to phenol and acetone—Stage 3—that is performed in a manner similar to the traditional Reaction/Stage 2 of FIG. 1. However, the new process comprises only two new additional stages of (1) separation of DMBA and AP from CHP by a method of continuous adsorption-desorption (New Stage 2), and (2) hydrogenation of DMBA separated from oxidation products at New Stage 2 to cumene (New Stage 4). Thus, the improved process utilizes only four stages instead of seven required in a conventional process.

Furthermore, due to DMBA separation from cumene oxidation products, at the stage of CHP cleavage (New Stage 2, FIG. 3): (1) there are no side-reactions to form AMS, AMS dimers, o- and p-cumene phenols (i.e. complex phenols) and other numerous by-products (i.e. no phenol tar is formed); (2) CHP cleavage reaction occurs at 100% selectivity; and (3) the CHP cleavage process (due to lack of presence of tar) on heterogeneous or homogeneous catalysts can operate in a much safer manner because the absence of DMBA enables the CHP cleavage process to be conducted in a "softer" regime and at lower temperatures.

Figure 4:
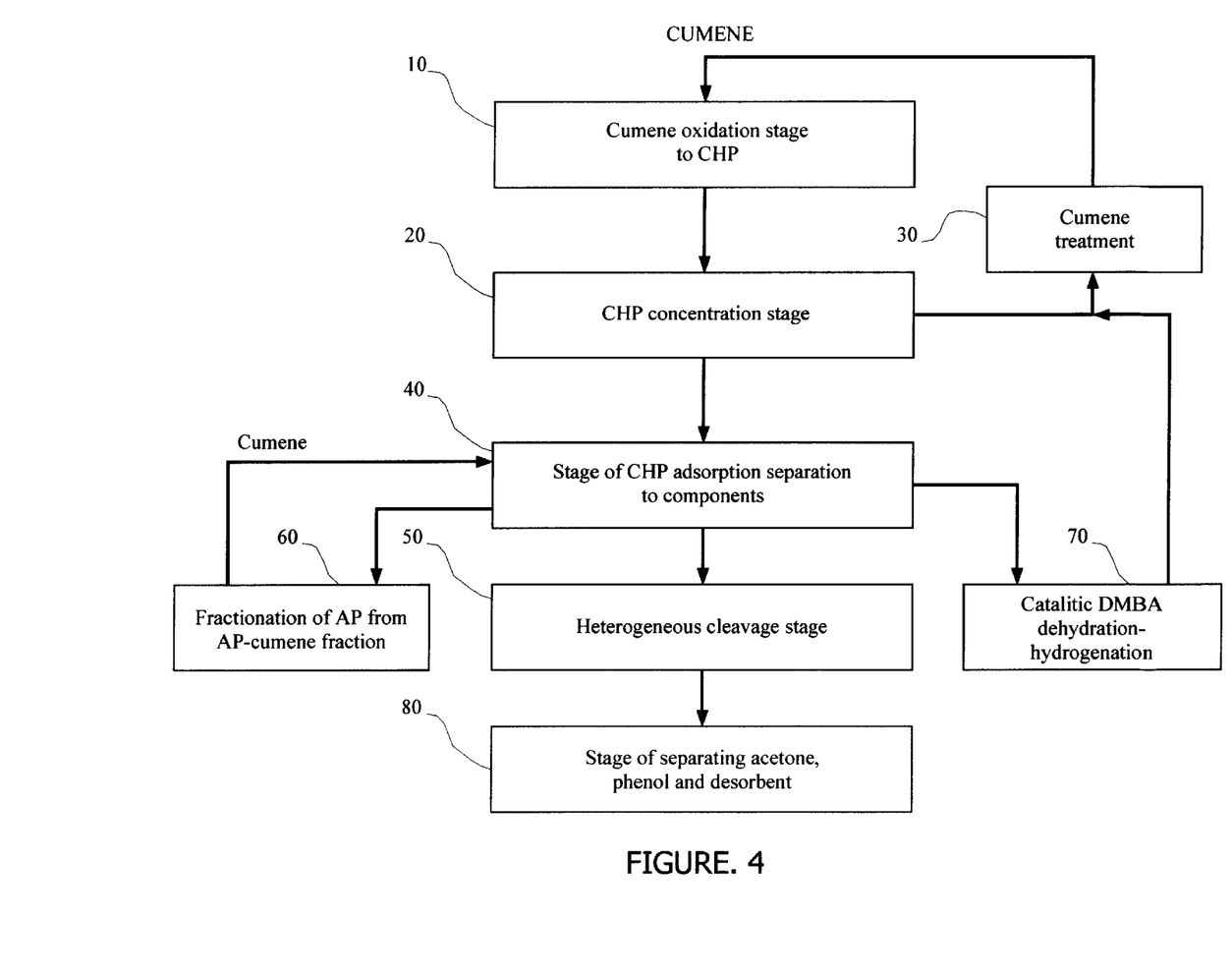
FIG. 4 schematically shows a diagram of the improved process for producing phenol and acetone via the cumene method in accordance with the present invention.

The improved process of the present invention is shown in FIG. 4. The improved process for producing phenol and acetone in accordance with the present invention comprises a stage 10 of cumene hydroperoxide production via cumene oxidation, a stage 20 of cumene oxidation products concentration to produce technical cumene hydroperoxide and recycle of unreacted cumene to oxidation stage after treatment 30, a stage 40 of separation of cumene oxidation products in a continuous or cycle adsorption-desorption utilizing predetermined adsorbents and desorbents, a stage 50 of heterogeneous cumene hydroperoxide cleavage with the use of acidic catalysts to produce at least phenol and acetone, a stage 60 of AP fractionation from AP-cumene fraction and return of cumene to the stage 40 (or, optionally, to stage 10), a stage 70 of catalytic DMBA direct hydrogenation, and a stage 80 of separating phenol, acetone, and desorbent to produce required product phenol and acetone.

Studies conducted during the development of the improved process show that heterogeneous and homogenous one-stage cleavage technologies cannot be used at high selectivity when using technical CHP with conventional composition and containing DMBA, due to principle differences (approximately 200 times) in the CHP cleavage rate and DCP cleavage rate (DCP being formed from DMBA and CHP). However, such heterogeneous or homogenous one-stage technologies may be utilized in the process of the present invention with the use of acidic catalysts with a wide spectrum of effectiveness.

Preferably, the main catalysts at the stage 50 of heterogeneous/homogeneous CHP cleavage are selected from at least the following:

protonic and aprotonic acids on supports, for instance $H_3PO_4$ on aluminum oxide or kiselgur, $BF_3$ on aluminum oxide, $FP(O)OH)_2$ and/or $F_2P(O)OH$ or HF on oxides of Al, Si or Ti;

natural or synthetic alumosilicate catalyst of the general formula $(Al_2O_3)_m(SiO_2)_n(H_2O)_p$, mainly amorphous alumosilicates at a ratio of $SiO_2: Al_2O_3=0.1$ to 10 and crystalline alumosilicates (zeolites) at a ratio $SiO_2: Al_2O_3=3$ to 100.

Preferably the catalysts are used with weak Luis and Brensted acidic sites and total value of Hammet acidity function $H_0=0.3–1.05$ (0.3–0.8) and having the effective pore diameter of 20–40A. Homogenous acidic catalysts such as $H_2SO_4$, HCl, and others may also be utilized successfully and with high selectivity in the inventive process assuming that DMBA is absent from products arriving at the cleavage stage. However, changing CHP cleavage technology from homogeneous to heterogeneous, enables elimination of the neutralization stage and further eliminates related problems of salts removal from cleavage products.

As discussed above, the lack of DMBA in technical CHP enables elimination of numerous condensation reactions. Hence, the fractionation of cleavage products at stage 50 is substantially simplified as the only cleavage products are phenol and acetone. When no AP is present in technical CHP delivered to stage 40, the fractionation stage 60 is also simplified as AP reacts with phenol to form azeotrope that causes difficulties in their separation and, hence, large energy expenditures.

The above-described approach requires that CHP that is free from AP and DMBA is used. Conventional methods of oxidation product distillation do not provide technical CHP that is completely free from DMBA and AP. Furthermore, use of 100% CHP without any cumene is dangerous because the thermal stability of highly concentrated (>92% wt) CHP is reduced significantly.

The improved process of the present invention utilizes technical CHP which always contains a quantity of cumene, thus resolving the safety problems. The inventive method of separating technical CHP is completed via continuous or cyclic adsorption-desorption.

Adsorbents may be selected from, but are not limited to the following:
1. Entirely ion-exchanged zeolites having an inlet window of less than 6A in dimension;
2. Magnesium silicate;
3. Synthetic polymeric materials in macropore or gel state produced via polymerization of amines, amides, acrylamides or via polymerization of styrene and divinylbenzene;
4. Anionites in macropore or gel state comprising a polystyrene matrix prepared via polymerization of styrene or styrene and divinylbenzene, and/or polycondensate matrix prepared via condensation of amines or amides or acrylamides and wherein anion is the amine-group of general formula-N(R'R") where R'R" is a hydrogen atom or alkyl radical, or amide-group of general formula R'CON(R"R'") where R'R" and R" are hydrogen atom or alkyl radical.

Desorbents may be selected from, but are not limited to the following:
1. Aromatic hydrocarbon $C_6$–$C_{22}$;
2. Ketones $C_3$–$C_6$;
3. Glycols $C_2$–$C_6$;
4. Mixture of water and acetone;
5. Water.

The aim is to produce, after desorption, the mixtures of acetophenone-light impurities of cumene oxidation products-desorbent, DMBA-desorbent, CHP-desorbent, and DCP-desorbent. The applied desorbents are separated from DMBA, AP and CHP and directed to recycle to adsorption-desorption stage 40 or, if cumene is used as a desorbent, it is recycled either to adsorption-desorption stage 40 or to cumene oxidation stage 10.

Preferably, CHP as free as possible from DMBA, AP and DCP is used as a feed to cleavage stage 50. At the CHP cleavage stage 50, $H_2SO_4$ may be used as a catalyst. The most preferable heterogeneous acidic catalyst is the acidic catalyst with Hammet acidity function Ho $=0.3–1.05$ (0.3–0.8) and effective pore diameter 20–40A.

If other catalysts are used, it is more preferable to use heterogeneous catalysts at CHP cleavage stage 50 that may be selected from, but are not limited to, the following:
1. protonic and aprotonic acids on support, for instance $H_3PO_4$ on aluminum oxide or kiselgur, $BF_3$ on aluminum oxide, $FP(O)OH)_2$ and/or $F_2P(O)OH$ or HF on oxides of Al, Si or Ti;
2. natural or synthetic alumosilicate catalyst of the general formula $(Al_2O_3)_m(SiO_2)_n(H_2O)_p$, mainly amorphous alumosilicates at a ratio of $SiO_2/Al_2O_3/ H2O=(1:0.1:0.1)–(1:10:10)$ and crystalline alumosilicates (zeolites) at a ratio $SiO_2/Al_2O_3/H2O=(1:3:1)–(1:100:10)$.

It is preferable to direct DMBA separated from cumene oxidation products to the stage 70 of catalytic direct hydrogenation to convert it into cumene with further cumene recycle to the cumene oxidation stage 10 after treatment 30. It is further preferable to carry out the process of DMBA direct hydrogenation to cumene at stage 70 in presence of catalysts selected from the following: Pd, Fe, Pt, Cu and/or Ag on aluminum oxide and at temperature 70–30° C. and hydrogen pressure of 5–40 atm.

In summary the inventive and distinctive features of the process of the present invention include, but are not limited to, the following:
1. Separation of DMBA and AP from CHP;
2. Elimination of formation of by-products at the CHP cleavage stage and the fractionation stage;
3. Direct hydrogenation of DMBA into cumene;
4. Simplification and reduced complexity of CHP cleavage products fractionation (i.e. the number of rectification columns at the fractionation stage can be reduced by a factor of 2 in accordance with the present invention as compared to the conventional scheme); and
5. A significant decrease in energy expenses compared to the conventional scheme (by a factor of approximately 1.5–2).

The above-described advantages and distinctions of the present invention are illustrated by Examples 2–4. Example 1 illustrates a prior art approach to production of acetone and phenol using the cumene method and is presented for comparative purposes only. It should be noted that the below described examples are presented for illustrative purposes only and are not intended to limit the scope of the present invention.

EXAMPLE 1 (comparative)

Cumene is oxidized in a cascade of bubbling reactors. By this oxidation 100 kg of the reaction oxidation mass (ROM) have been produced with the following composition: wt. %

| | |
|---|---|
| Cumene | 73.117 |
| AP | 0.186 |
| DMBA | 1.206 |
| CHP | 25.409 |
| DCP (dicumyl peroxide) | 0.082 |
| Organic acids | 3000 ppm |

Selectivity at the oxidation stage is 94% theoretical. The produced ROM is passed to the 3-step stage of CHP concentration to obtain CHP final concentration of 92–93%. As a result, technical CHP is produced with the following composition: cumene-1.53 wt. %, AP-0.69 wt. %, DMBA-4.45 wt. %, CHP-93.1 wt. %, DCP-0.3 wt. %. Impurities including organic acids are 3000 ppm. The selectivity reduction at the CHP concentration stage is 0.3% abs. The technical CHP with said composition is supplied to the CHP cleavage stage according to the method specified in U.S. Pat. No. 5,254,751.

As a result, CHP cleavage products (phenol and acetone) as well as by-products (dicumyl peroxide (DCP), cumylphenol (CP), AMS dimers) and micro-impurities (hydroxyacetone, mesityl oxide, organic acids ($C_1$–$C_2$)) are produced.

The composition of the reaction cleavage mass (RCM) is as follows: wt. %

| | |
|---|---|
| Phenol | 56.47 |
| Acetone | 35.00 |
| AMS | 3.19 |
| DCP (dicumyl peroxide) | 0.9 |
| DMBA | 0.26 |
| AP | 0.59 |
| CP | 0.55 |
| Dimers | 0.36 |
| Organic acids | 3000 ppm |
| Mesityl oxide | 500 ppm |
| Hydroxyacetone | 1500 ppm |

The yield of AMS, a valuable by-product, is 80% theoretical. The cumene consumption per 1 t phenol after the cleavage stage is 1300 kg. Sulfuric acid in the ROM is neutralized by sodium hydroxide.

To improve the removal of salts formed, the RCM is watered to a water concentration of about 7–12 wt. % and the products are passed to the stage of their fractionation comprising 8 fractionation columns (in a typical well-known configuration):
1. The RCM is passed into column 1 wherein it undergoes a separation into acetone and phenol streams.
2. The acetone stream containing acetone, water, cumene, AMS, aldehydes and a little phenol is passed into column 1 wherein the basic amount of aldehydes is distilled away.
3. The acetone stream which is already practically free of aldehydes is passed into column 3 where product acetone is produced (a hydrocarbon fraction containing cumene and AMS goes from the column bottom).
4. The phenol stream containing phenol, a few percent of hydrocarbons (cumene and AMS), AP, CP, AMS dimers, and such impurities as mesityl oxide, hydroxyacetone, 2-MBF, is passed into column 4 wherein phenol is separated from heavy products—AP, CP, AMS dimers.
5. Crude phenol is passed into column 6 to which water is also supplied. In this column crude phenol is treated from hydrocarbons and 2-MBF.
6. Phenol which is practically free of hydrocarbons and 2-MBF but containing hydroxyacetone and mesityl oxide as impurities is passed to ion-exchange resin (IER) purification which results in hydroxyacetone and mesityl oxide removal.
7. After the IER purification phenol is passed into column 7—the product phenol column.
8. Phenol tar produced at the bottom of column 4 is passed into column 8 where additional phenol distillation from phenol tar occurs.
9. Phenol tar produced at the bottom of column 8 is passed to cracking to produce phenol and AMS or is utilized.

As a result of side reactions in the bottoms of fractionation columns, the AMS yield is reduced to 78%, the consumption coefficient of cumene/phenol is increased to 1333 kg/t, and the waste yield of phenol tar is increased to 56 kg/t. Thus the raw material losses at the fractionation stage due to chemical reactions are about 20–30 kg/t.

As described above, phenol tar from column 4 bottom is passed into the reactor of its thermal cracking. The rate of tar conversion into useful products is below 40% since an increase of the conversion depth will result in coke-like untransportable products formation. The useful products formed in the thermal cracking—phenol and AMS—are recycled to the fractionation stage. As a result of the phenol tar partial cracking the phenol tar yield is reduced to 32–40 kg/t and the cumene consumption value reaches about 1310 kg/t of phenol.

Unconverted phenol tar is passed to incineration to produce steam. Therefore the process is characterized by the following parameters:
1. Cumene/phenol consumption after the CHP cleavage stage—1305 kg/t of phenol;
2. AMS yield after the CHP cleavage stage—80% theoretical;
3. phenol tar yield after the CHP cleavage stage—35 kg/t of phenol;
4. cumene/phenol consumption after the fractionation stage—1333 kg/t of phenol;
5. AMS yield losses after the fractionation stage;
6. cumene/phenol consumption after the phenol tar cracking—1310 kg/t of phenol;
7. phenol tar yield—35 kg/t of phenol;
8. steam consumption per 1 t of phenol—4 t.

EXAMPLES 2-A to 2-T

Examples 2-A to 2-P were preformed using a variety of combinations of adsorbents and desorbents. Examples 2-Q to 2-T were performed similarly to Examples 2-A to 2-P, except that a variety of different acidic catalysts were used. Cumene was oxidized as in Example 1 and the reaction oxidation mass (ROM) was produced with the same composition as described in Example 1. The produced ROM was passed to the first step of the CHP concentration stage. CHP was concentrated to its concentration in technical CHP no less than 40 wt. %.

As a result, 100 kg of technical CHP was produced with the following composition: wt. %

| | |
|---|---|
| Cumene | 57.68 |
| AP | 0.29 |
| DMBA | 1.90 |

-continued

| | |
|---|---|
| CHP | 40.00 |
| DCP | 0.13 |

There were no selectivity losses at the CHP concentration stage. The technical CHP having the said composition was passed to the continuous adsorption-desorption stage 40 wherein in Example 2-A polyamide was used as an adsorbent and cumene was used as a desorbent.

In the end of the continuous adsorption-desorption process the following fractions are produced (in kg)

| | |
|---|---|
| Cumene-light ($CH_3OH$, organic acids)-AP | 60.0 (cumene content-99.96 wt. %) |
| Cumene-DMBA | 23.4 (cumene content-87.32 wt. %) |
| Cumene-CHP | 41.5 (cumene content-10.63 wt. %) |
| Cumene-DCP | 0.1 (cumene content-9.75 wt. %) |

In Examples 2-B to 2-P, the following parameters were used:

Example 2-B: Magnesium silicate is used as an adsorbent. At the end of the continuous adsorption-desorption process the fractions similar to Example 2-A are produced.

Example 2-C: Synthetic polymeric materials produced by amines polymerization are used as an adsorbent. At the end of the continuous adsorption process the fractions similar to Example 2-A are produced.

Example 2-D: Synthetic polymeric materials produced by amides polymerization are used as an adsorbent. At the end of the continuous adsorption process the fractions similar to Example 2-A are produced.

Example 2-E: Synthetic polymeric materials produced by acrylamides polymerization are used as an adsorbent. At the end of the continuous adsorption process the fractions similar to Example 2-A are produced.

Example 2-F: Synthetic polymeric materials produced by styrene and divinylbenzene polymerization are used as an adsorbent. At the end of the continuous adsorption process the fractions similar to Example 2-A are produced.

Example 2-G: Anionites (being a polystyrene matrix) are used as an adsorbent. At the end of the continuous adsorption process the fractions similar to Example 2-A are produced.

Example 2-H: Anionites (being a polycondensate matrix) made by amines condensation are used as an adsorbent. In the amines condensation the exchanged anion is an aminogroup with a common formula—$N(R'R'')$ wherein $R'$ and $R''$ are a hydrogen atom or an alkyl radical. At the end of the continuous adsorption process the fractions similar to Example 2-A are produced.

Example 2-I: Anionites (being a polycondensate matrix) made by acrylamides condensation are used as an adsorbent. In the acrylamides condensation the exchanged anion is an amino group $R'CON(R''R''')$ wherein $R'$, $R''$ and $R'''$ are a hydrogen or alkyl atom. At the end of the continuous adsorption process the fractions similar to Example 2-A are produced.

Example 2-J: Totally ion-exchanged zeolites with an inlet window of dimension 6–40 Å are used as a desorbent.

Example 2-K: Anionites in a gel or macroscopic state (being a polycondensate matrix) made by amines condensation are used as an adsorbent.

Example 2-L: Similar to Examples 2-A to 2-K, but aromatic hydrocarbons $C_6$–$C_{22}$ are used as a desorbent.

Example 2-M: Similar to Examples 2-A to 2-K, but a mixture of water and acetone is used as a desorbent.

Example 2-N: Similar to Examples 2-A to 2-K, but water is used as a desorbent.

Example 2O: Similar to Examples 2-A to 2-K, but ketones $C_3$–$C_6$ are used as a desorbent.

Example 2-P: Similar to Examples 2-A to 2-K, but glycols $C_2$–$C_6$ are used as a desorbent.

Figure 5:
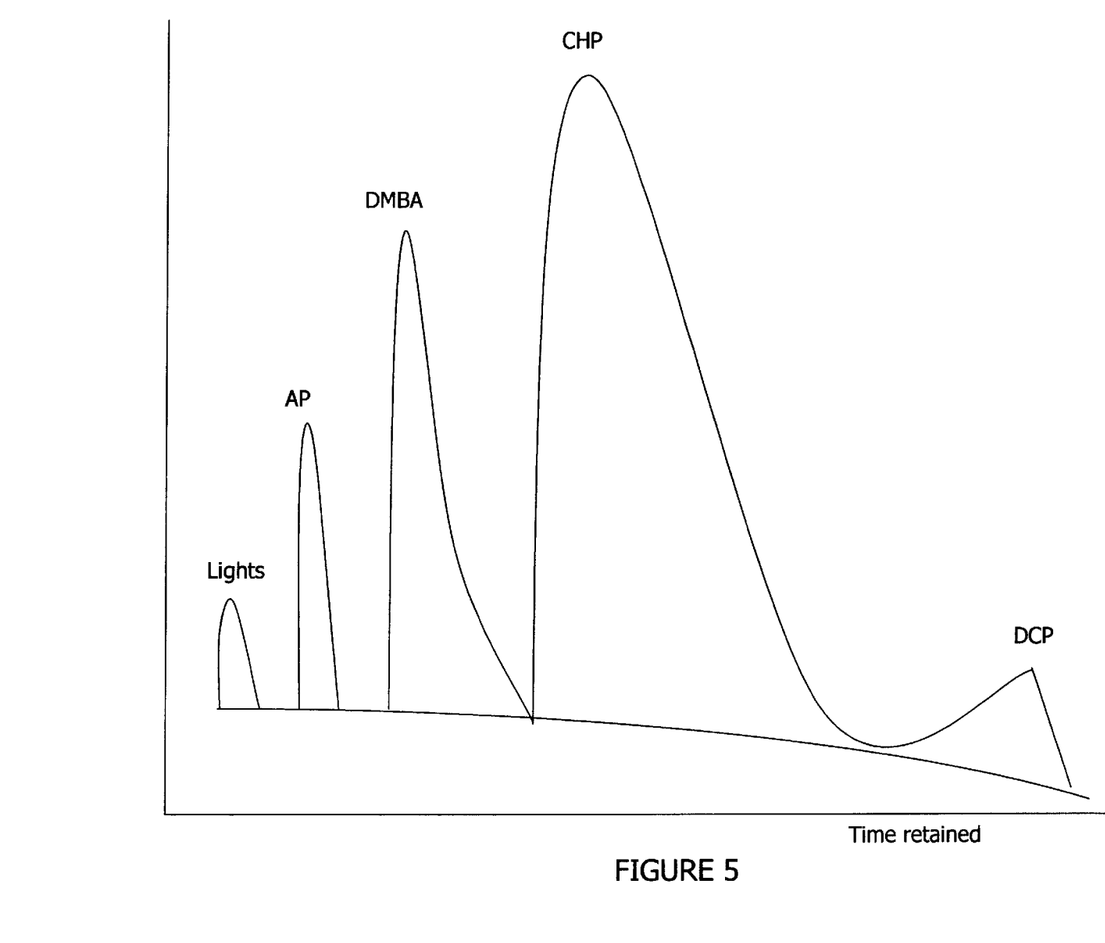
FIG. 5 is a liquid separation chromatogram for experimental Example 2-A in accordance with the process of FIGS. 3 and 4 using cumene as an adsorbent.

The component separation degree is close to 100% in each case. Liquid separation chromatogram for Example 2-A using cumene as a desorbent is shown in FIG. 5. The cumene—"lights" (aldehydes, organic acids, methanol and others) and AP fraction are passed to separation 60 by the standard fractionation method. The "lights" are taken off as an overhead product and the produced fraction containing "lights" and 0.1 kg cumene is burnt up. Cumene is produced in an amount of 59.88 g as a side-draw and recycled to the oxidation stage 10. In the column bottom pure phenol, which is a commercial product, is produced in an amount of 0.29 kg. The produced acetophenone can be hydrogenated to produce ethylbenzene which is also a commercial product. The binary cumene-DMBA fraction produced at the continuous adsorption-desorption stage is passed to the catalytic dehydration-hydrogenation stage 70 to convert DMBA into cumene.

In Example 2-A, $Pd/Al_2O_3$ was used as a catalyst. The process was carried out at a temperature of 130° C., a hydrogen pressure of 6 atm. DMBA conversion was 100%, selectivity was 99.9%.

In Example 2-B, $Fe/Al_2O_3$, $Pt/Al_2O_3$, $Cu/Al_2O_3$ and $Ag/Al_2O_3$ were used as a catalyst. When using these catalysts the temperature was varied in the range of 70–300° C., and the pressure—5–40 atm. As a result of the process being carried out on these catalysts, the DMBA conversion was 100%, selectivity was 99.9%.

The cumene produced in an amount of 14.98 kg after standard treatment, is passed to the stage 10 of cumene oxidation into cumene hydroperoxide.

The binary cumene-CHP fraction produced at the continuous adsorption-desorption stage 40 in an amount of 44.89 kg is passed to the acidic cleavage stage 50. Sulfuric acid, a conventional catalyst, can be used as an acidic catalyst, so that the process is carried out according to conventional scheme as described in U.S. Pat. No. 5,254,751.

As a result of CHP cleavage at a temperature of 55° C., phenol in an amount of 24.73 kg and acetone—15.27 kg were produced. There were no DCP, AMS dimers, cumylphenol, AMS, DMBA or AP in the cleavage products. Furthermore, there were no deep condensation products in the cleavage products. The CHP cleavage products were passed to the stage of their fractionation. The fractionation is performed according to a well-known 3-column scheme.

Heterogeneous acidic catalysts such as (Example 2-A) synthetic zeolites in $H^+$-form with the ratio $SiO_2/Al_2O_3$=8.5 can be used at the CHP cleavage stage 50 as acidic catalysts. As a result of the cleavage, phenol in an amount of 24.7 kg and acetone in the amount of 15.2 kg were produced.

Examples 2-Q to 2-T were conducted similarly to Examples 2-A to 2-P, except that a different set of heterogeneous catalysts was used in each example. Table 1 below summarizes the wide variety of heterogeneous catalysts that were used.

TABLE I

| Heterogeneous catalysts of DMBA and AP free CHP cleavage | | |
|---|---|---|
| Example 2-Q | Protonic acids on supports | |
| 1. | H₃PO₄ on | Al₂O₃ |
| 2. | H₃PO₄ on | Kieselguhr |
| 3. | HF on | Al₂O₃ |
| 4. | HF on | SiO₂ |
| 5. | HF on | TiO₂ |
| Example 2-R | Aprotonic acids on supports | |
| 1. | BF₃ on | Al₂O₃ |
| 2. | FP (O)(OH)₂ on | Al₂O₃ |
| 3. | F₂P | Al₂O₃ |
| Example 2-S | Amorphous aluminosilicates with the ratio Si/Al in the range 0.1–10 | |
| 1. | Ratio Si/Al = 0.1 | |
| 2. | Ratio Si/Al = 10 | |
| Example 2-T | Crystalline alumosilicates (zeolites) with the ratio Si/Al in the range 3–10 | |
| 1. | ratio Si/Al = 3 | |
| 2. | ratio Si/Al = 10 | |

The produced cumene/DCP fraction in an amount of 0.1 kg was passed to fractionation and the production of commercial DCP being used as a polymerization initiator. Cumene separated from the cumene/DCP fraction was passed to the stage 10 of its oxidation.

In the end of the process according to Examples 2-A to 2-T the following were produced:

| | |
|---|---|
| Phenol | 24.73 kg (selectivity 100%) |
| Acetone | 15.27 kg (selectivity 100%) |
| Acetophenone | 0.29 kg |
| DCP | 0.13 kg |
| Phenol tar | None |

Cumene consumption was 1278 kg/t of phenol.
Steam consumption was 2 t per 1 t of phenol.

EXAMPLE 3

Cumene was oxidized as in Example 1 and the reaction oxidation mass (ROM) was produced with the same composition as described in Example 1. The produced ROM was passed to the two-stage CHP concentration (stage 20). CHP was concentrated to its concentration in technical CHP no less than 60 wt. %.

As a result, 100 kg of technical CHP was produced with the following composition: wt. %

| | |
|---|---|
| Cumene | 36.52 |
| AP | 0.44 |
| DMBA | 2.85 |
| CHP | 60.00 |
| DCP | 0.19 |

Selectivity losses at the CHP concentration stage were 0.1% abs.

The fractionation of the technical CHP having the above composition was performed as in Example 2-A.

In the end of the continuous adsorption-desorption process the following fractions were produced: (in kg)

| | |
|---|---|
| Cumene-light hydrocarbons (CH₃OH, organic acids)-AP | 46.28 (cumene content-99.05 wt. %) |
| Cumene-DMBA | 10.75 (cumene content-73.5 wt. %) |
| Cumene-CHP | 66.76 (cumene content-10.12 wt. %) |
| Cumene-DCP | 0.21 (cumene content-9.73 wt. %) |

The separation of cumene-lights-AP fraction was performed as in Example 2-A. As a result of the separation, AP in an amount of 0.44 kg and cumene—45.74 kg were produced. 0.1 kg cumene and "lights" taken off as an overhead product and were passed to incineration. The produced cumene was recycled to the oxidation stage 10.

The dehydration-hydrogenation of the binary cumene-DMBA fraction was performed as in Example 2-A. DMBA conversion was 100%, selectivity is 99.9%.

The cumene produced in an amount of 10.75 kg after standard treatment was passed to the stage 10 of cumene oxidation into cumene hydroperoxide.

The separated binary cumene-CHP fraction in an amount of 66.76 kg was passed to the stage 50 of acidic heterogeneous cleavage as in Examples 2-Q to 2-T.

As a result of CHP cleavage, phenol in an amount of 37.1 kg and acetone—22.9 kg were produced.

With no DMBA, the cleavage stage selectivity was 100%. There were no DCP, AMS dimers, cumyl-phenol, AMS, DMBA or AP in the cleavage products. There were no deep condensation products in the cleavage products as well. The CHP cleavage products were passed to the stage of their fractionation. The fractionation was performed according to a 3-column scheme.

The produced cumene/DCP fraction in an amount of 0.21 kg was passed to fractionation and the production of commercial DCP being used as a polymerization initiator etc. Cumene produced from the cumene/DCP fraction was passed to the stage 10 of its oxidation.

In the end of the process according to Example 3 the following were produced:

| | |
|---|---|
| Phenol | 37.1 kg (selectivity 100%) |
| Acetone | 22.9 kg (selectivity 100%) |
| Acetophenone | 0.44 kg |
| DCP | 0.19 kg |
| Phenol tar | No |

Cumene consumption was 1279 kg/t of phenol.
Steam consumption was 2.05 t per 1 t of phenol.

EXAMPLE 4

Cumene was oxidized as in Example 1 and the reaction oxidation mass (ROM) was produced with the same composition as described in Example 1. The produced ROM was passed to the three-step stage of CHP concentration (stage 20). CHP was concentrated to its concentration in technical CHP no less than 8,0 wt. %.

As a result, 100 kg of technical CHP was produced with the following composition: wt. %

| | |
|---|---|
| Cumene | 1.53 |
| AP | 0.68 |
| DMBA | 4.39 |

| | |
|---|---|
| CHP | 93.10 |
| DCP | 0.30 |

Selectivity losses at the CHP concentration stage were 0.3% abs.

The fractionation of the technical CHP having the above composition was performed as in Example 2-A. In the end of the continuous adsorption-desorption process, the following fractions were produced: wt. %

| | |
|---|---|
| Cumene-light hydrocarbons (CH$_3$OH, organic acids)-AP | 10.87 (cumene content-93.8 wt. %) |
| Cumene-DMBA | 11.63 (cumene content-62.3 wt. %) |
| Cumene-CHP | 102.88 (cumene content-9.51 wt. %) |
| Cumene-DCP | 0.33 (cumene content-9.00 wt. %) |

The separated binary cumene-lights-AP fraction was passed to separation by the standard fractionation method. As a result of the separation, AP in an amount of 0.68 kg and cumene—9.19 kg were produced. The produced cumene was recycled to the oxidation stage. 0.1 kg cumene, and "lights" taken off as overhead products were passed to incineration.

The separated binary cumene-DMBA fraction, avoiding fractionation, was passed to the catalytic DMBA hydrogenation stage 70 to convert DMBA into cumene. The process was performed as in Example 2-A. DMBA conversion was 100%, selectivity was 99.99%.

The cumene produced in an amount of 11.63 kg after standard treatment was passed to the stage 10 of cumene oxidation into cumene hydroperoxide. The separated binary cumene-CHP fraction in an amount of 102.88 kg was passed to the stage of acidic cleavage. Synthetic zeolites HY were used as acidic catalysts as in Examples 2-Q to 2-T.

As a result of CHP cleavage, at a temperature of 55° C. phenol in an amount of 57.57 kg and acetone in the amount of 35.52 kg were produced. With no DMBA, the cleavage stage selectivity was 100%. There were no DCP, AMS dimers, cumyl-phenol, AMS, DMBA or AP in the cleavage products. There were no deep condensation products in the cleavage products.

The CHP cleavage products were passed to the stage of their fractionation. The fractionation was performed according to a 3-column scheme. The produced cumene/DCP fraction in an amount of 0.33 kg was passed to fractionation and the production of commercial DCP being used as a polymerization initiator etc.

Cumene produced from the cumene/DCP fraction is passed to the stage 10 of its oxidation. In the end of the process according to Example 4, the following were produced:

| | |
|---|---|
| Phenol | 57.57 kg (selectivity 100%) |
| Acetone | 32.52 kg (selectivity 100%) |
| Acetophenone | 0.68 kg |
| DCP | 0.30 kg |
| Phenol tar | No |

Cumene consumption was 1280 kg/t of phenol.
Steam consumption was 2.1 t per 1 t of phenol.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. A method for producing phenol and acetone comprising the steps of:

(a) producing cumene hydroperoxide via cumene oxidation;

(b) concentration of cumene oxidation products to produce technical cumene hydroperoxide;

(c) recycling unreacted cumene produced at said step (b) to said step (a);

(d) performing cumene oxidation products separation via a continuous cyclic adsorption-desorption with the use of at least one adsorbent and at least one desorbent;

(e) performing cumene hydroperoxide cleavage using at least one acidic catalyst to produce cleavage products; and (f) performing cleavage products fractionation to produce phenol and acetone.

2. The method of claim 1, wherein said at least one adsorbent is selected from a group of:

entirely ion-exchanged zeolites having an inlet window of dimension less than about 6A, magnesium silicate, synthetic polymeric materials that are in a macropore or gel state produced via polymerization of amines, amides, acrylamides or via polymerization of styrene and divinylbenzene, anionites in macropore or gel state being a polystyrene matrix prepared via polymerization of one of styrene, and styrene and divinylbenzene, and polycondensate matrix prepared via condensation of amines or amides or acrylamides, and wherein anion is an amine-group of general formula —N(R'R") where R'R" is one of a hydrogen atom, alkyl radical, and amide-group, of general formula R'CON(R"R'") where R'R" and R'" are one of a hydrogen atom and an alkyl radical.

3. The method of claim 1 wherein said at least one desorbent is selected from a group of: aromatic hydrocarbons $C_6$–$C_{22}$, ketones $C_3$–$C_6$, glycols $C_2$–$C_6$, the mixture of water and acetone, and water, further comprising the step of:

(g) using said at least one desorbent to produce mixtures of acetophenone-light impurities of cumene oxidation products-desorbent, DMBA-desorbent, CHP-desorbent, and DCP-desorbent.

4. The method of claim 3, further comprising the steps of:

(h) separating said at least one desorbent from dimethylbenzene alcohol, acetophenone and cumene hydroperoxide;

(i) recycling said at least one desorbent to said step (d); and (j) when cumene is used as said at least one desorbent, recycling cumene to one of said step (a) and said step (d).

5. The method of claim 1, further comprising the step of:
(k) feeding cumene hydroperoxide substantially free from dimethyl benzene alcohol, acetophenone and dicumylperoxide to said step (e).

6. The method of claim 1, wherein said at least one acidic catalyst comprises sulfuric acid.

7. The method of claim 5, wherein said at least one acidic catalyst is selected from:
protonic and aprotonic acids on supports including:
$H_3PO_4$ on one of aluminum oxide, and kiselgur; $BF_3$ on aluminium oxide;
one of FP(O)OH and HF on one of aluminium, silicium and titanium oxides;
natural and synthetic alumosilicate catalysts of general formula $(Al_2O_3)_m(SiO_2)_n(H_2))_h$ including:
alumosilicates at a ratio of $SiO_2$ to $Al_2O_3$ to $H_2O$ of (1:0.1:0.1)–(1:10:10), and
crystalic alumosilicates (zeolites) at a ratio of $SiO_2$ to $Al_2O_3$ to $H_2O$ of (1:3:1)–(1:100:10).

8. The method of claim 7, wherein said at least one acidic catalyst is selected from heterogeneous acidic catalysts with the Hammet acidity function $H_0$=0.3–0.8 and pore diameter of about 20–40A.

9. The method of claim 1, further comprising the steps of:
(l) separating dimethyl benzene alcohol from cumene oxidation products at said step (d);
(m) performing catalytic hydrogenation on said dimethyl benzene alcohol to convert said dimethyl benzene alcohol into cumene; and
(n) recycling said cumene to said step (a).

10. The method of claim 9, wherein said step (m) is conducted in the presence of at least one catalyst selected from: Pd, Fe, Pt, Cu and Ag on aluminium oxide, and wherein said step (m) is conducted at a temperature of about 70–300° C. and hydrogen pressure of about 5–40 atm.

11. The method of claim 1, wherein said step (c) further comprises the step of treating said recycled cumene prior to delivering said cumene to said step (a).

* * * * *